May 4, 1954 H. A. MOLTENI ET AL Re. 23,823
DETERGENT AND METHOD OF MAKING THE SAME
Original Filed March 9, 1950
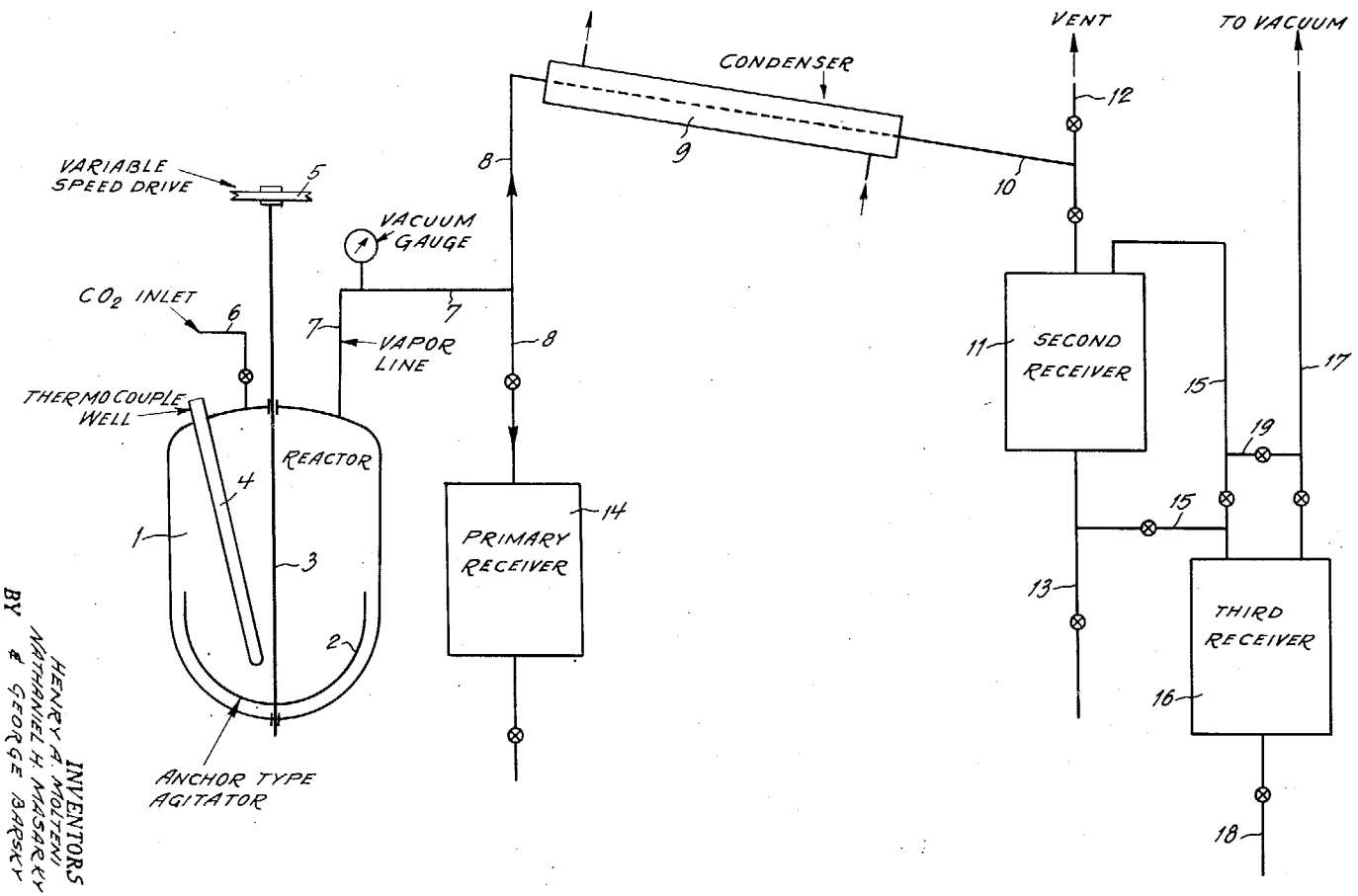
INVENTORS
HENRY A. MOLTENI
NATHANIEL H. MASARKY
& GEORGE BARSKY
BY
ATTORNEY Reissued May 4, 1954 Re. 23,823

UNITED STATES PATENT OFFICE 23,823

DETERGENT AND METHOD OF MAKING THE SAME

Henry A. Molteni, Dover, and Nathaniel H. Masarky, Teaneck, N. J., and George Barsky, New York, N. Y., assignors to E. F. Drew & Co., Inc., New York, N. Y., a corporation of Delaware Original No. 2,635,103, dated April 14, 1953, Serial No. 148,692, March 9, 1950. Application for reissue June 17, 1953, Serial No. 362,430

8 Claims. (Cl. 260—400)

Matter enclosed in heavy brackets [ ] appears in the original patent but forms no part of this reissue specification; matter printed in italics indicates the additions made by reissue.

The present invention is directed to detergents and more particularly to synthetic detergents and compositions containing the same, and methods of making such detergents.

The present invention has among its objects the provisions of a method of making condensation products usable for detergent purposes which is simple and highly effective, and is adapted to large scale operation with controllable and reproducible results.

It is also among the objects of the present invention to provide a condensation product which is stable, light in color, highly resistant to rancidity and having excellent detergent properties.

It is further among the objects of the present invention to provide a shampoo composition including said condensation product which is smooth, stable over a long period of time under adverse conditions and highly effective in its detergent properties.

It is still further among the objects of the present invention to provide a detergent in the form of a cake, which is coherent and does not disintegrate on handling, which is sufficiently soluble to enable its use in ordinary washing operations and which may be readily produced on a large scale.

In practicing the present invention there is provided a water-soluble salt of [hydroxyethylsulphuric] *hydroxyethylsulphonic* acid. This is mixed with a fatty acid or a mixture of fatty acids and preferably the higher saturated fatty acids. For example, one may use the fatty acids obtained by hydrolysis of coconut oil or may take certain fractions of such fatty acids. The fatty acids include lauric, [hydristic] *myristic*, palmitic and stearic. Preferably saturated higher fatty acids having at least 12 carbon atoms are used and sometimes it may be advisable to avoid the presence of any substantial amount of the unsaturated fatty acids; in such case, the fatty acids have an iodine number of not over 2.0.

The relative proportions of the constituents are such that there is present for each mol. of the [hydroxyethylsulphuric] *hydroxyethylsulphonic* acid salt an amount of the fatty acid which is less than 1 mol., say 0.95 mol., and more than 0.6 mol. The mixture is heated in a closed reaction kettle while maintaining an inert atmosphere by the use of a suitable gas such as nitrogen or carbon dioxide. The heating is conducted at a temperature of about 200° to 300° C. for a sufficient length of time to complete the reaction between the constituents. Usually from 1 to 4 hours is sufficient. A pressure is maintained which is usually somewhat below atmospheric but in all cases above 250 mm. After the substantial completion of the reaction the pressure is reduced to below 100 mm. and preferably to as low a point as practical in ordinary production equipment, say, from 10 to 20 mm. The heating is continued for a sufficient length of time at the high vacuum to volatilize and remove any unreacted fatty acid present in the reaction product. It is desirable that the product have a very low free fatty acid number, say, not over 5.0 and often as low as 2.0.

Usually a considerable excess of the [hydroxyethylsulphuric] *hydroxyethylsulphonic* acid salt is used and it may be desirable to remove such excess from the reaction product. This can be accomplished by dissolving the reaction product in water and recrystallizing the same by usual methods, whereby the [hydroxyethylsulphuric] *hydroxyethylsulphonic* acid salt remains, in solution. By this procedure it is found that the final product is dry and granular, and is nonhydroscopic.

In the accompanying drawing constituting a part hereof and in which like reference characters indicate like parts, the single figure is a diagrammatic view of an apparatus which may be used in practicing the present invention.

The reactor 1 is a closed vessel having a stirrer 2 therein mounted on a vertical shaft 3, the reactor having a well 4 therein for a thermocouple or the like. A driving means 5 is provided for rotating the stirrer. The reactor is provided with an inlet 6 for carbon dioxide and an outlet 7 for vapors produced in the reaction.

Vapors pass through vertical pipe 8 into condenser 9, which may be water cooled, the condensate passing out of the condenser through line 10 and into a receiver 11. Gases therefrom may be vented through pipe 12 and liquid from the receiver may be drained off through pipe 13. A receiver 14 is provided for the purpose of catching drippings from vapor lines 7 and 8.

Connections 15 from the top and bottom of receiver 11 lead into receiver 16 and outlet 17 therefrom is connected to a source of vacuum. Liquid from receiver 16 may be removed through pipe 18. A bypass 19 is provided from receiver 11 to the source of vacuum.

The following are examples of the operation of the invention.

Example 1

1 mol. of [hydroxyethylsulphuric] *hydroxyethylsulphonic* acid sodium salt and 0.8 mol. of a mixture of fatty acids in which lauric acid is the major constituent, containing not over 30% of the adjacent fatty acids and derived from the fractional distillation of the fatty acids of coconut oil, are heated in an atmosphere of carbon dioxide to 220° C.–260° C. and maintained at said temperature for 2 hours or more. The pressure is maintained at about 300 mm. absolute pressure or somewhat higher for the aforesaid period until the reaction is substantially complete. The pressure is then decreased as rapidly as possible to not over 20 mm. and maintained at said temperature so that the total elapsed time is at least 4 hours, of which about 1.5 hours is at the lowest pressure.

The mass is cooled as rapidly as possible with continuous agitation. As the cooling proceeds the physical condition of the reaction mass changes from a non-viscous liquid to a viscous mass and then to a brittle mass which granulates readily and forms powder or beads. After the contents of the reaction vessel have reached a relatively low temperature, say below 120° C., the mass may be removed. To further pulverize the mass to a uniform size, it is cooled to room temperature. The free fatty acid number of the product is approximately 5.0. During the entire operation oxygen is excluded from the reaction vessel.

To purify the product by removing unreacted salts, the product is dissolved in water to form a saturated solution at least 90° to 95° C. Water is evaporated to give a super-saturated solution and it is then cooled to room temperature. The product precipitates out and is separated from the mother liquor. If desired, the product may be washed with a limited amount of water. The crystallized product is substantially free from excess of [hydroxyethylsulphuric] *hydroxyethylsulphonic* acid compound.

Example 2

A mixture is made of 1 mol. equal to 148 lbs. of sodium hydroxy [ethysulphate] *ethylsulphonate* and .8 mol., equal to 175 lbs. of commercial lauric acid. Said acid is derived by the hydrolysis of hydrogenated coconut oil and fractional distillation thereof to give a lauric acid fraction, which contains a major portion of lauric acid and a minor portion of adjacent acids. A typical mixture has a free fatty acid number of 126 to 132, a maximum iodine value of 2.0, a titre of about 24° C. as a minimum, and a saponification value of 250 to 263.

The mixture is heated in the reactor to a temperature of 220° to 260° C. in an atmosphere of $CO_2$ and at approximately 400 mm. absolute pressure. The heating at this temperature is continued for 2 hours or more, after which the pressure is decreased rapidly to less than 20 mm. absolute pressure, while maintaining approximately the same range of temperatures. Temperature and low pressure are maintained for at least an hour and a half and sufficiently long so that the total time of heating is at least 4 hours.

Heating is then discontinued and the reaction mass is cooled rapidly while maintaining the agitation and the vacuum. When no more fatty acids distill over, the vacuum may be released. The reactor should not be open to the atmosphere until the temperature has dropped below about 120° C.

Example 3

A mixture is made of 1 mol. of sodium hydroxy

[ethylsulphate] *ethylsulphonate* equal to 111 lbs., with .8 mol. of commercial stearic acid, equal to 162 lbs. A typical stearic acid composition has a free fatty acid number of 99 to 105, a maximum iodine value of 3.0, a saponification value of 197 to 205, and a titre of 61° to 64° C. The procedure of Example 2 is followed.

Example 4

A mixture is made of 1 mol. of sodium hydroxy [ethylsulphate] *ethylsulphonate* and .8 mol. of commercial lauric acid. The acid is derived from coconut oil, as described in Example 2, the lower boiling fraction being separated from the lauric acid fraction. A typical composition has a free fatty acid number of 126 to 132, a saponification value of 251 to 263, an iodine value of 8 to 16 and a titre of 24° to 28° C. The procedure of Example 2 is followed.

Example 5

Any of the above compositions may be made into a cream shampoo. In making such a shampoo a stabilizing material is used and it is dispersed in water. Then a relatively large amount of the aforesaid product, which is the detergent, is added, together with salt and lanolin. The mixture is agitated with a suitable type of agitator and is simultaneously heated preferably on a steam bath to 50°–75° C. Agitation is continued until the composition is smooth and creamy. The composition while still at elevated temperature is homogenized in a suitable mixer for about 10 minutes, poured into containers and allowed to cool. The following is a typical composition in parts by weight:

| | |
|---|---|
| Polyvinyl alcohol | 2 |
| Water | 71 |
| Product of Example 2 | 23 |
| Product of Example 3 | 2 |
| Stearic acid (comm.) | 1 |
| Sodium chloride | 1 |
| Lanolin | 1 |

Example 6

The following composition is quite suitable as a shampoo, the parts being by weight:

| | |
|---|---|
| Methylcellulose | 0.5 |
| Arylalkylsulphonate (Na) | 0.5 |
| Water | 71.0 |
| Product of Example 2 | 23.0 |
| Product of Example 3 | 2.0 |
| Stearic acid | 1.0 |
| Sodium chloride | 2.0 |
| Sodium hydroxide | 0.14 |
| Lanolin | 1.0 |

Example 7

In order to produce the detergent in a bar or cake form any one of the reaction products of Examples 1 to 4 is heated to a point substantially above room temperature, say 50° to 100° C. 5 to 10 parts by weight of water at about the boiling point is mixed thoroughly therewith. When the composition is uniform it is cast in molds to form cakes of suitable size and shape. In a typical composition 9 parts of the condensation product may be mixed with 1 part of water to form a satisfactory cake. If desired, addition agents, fillers, abrasives, coloring materials, perfumes or the like may be introduced during the mixing operation.

The procedure is based upon the discovery that the condensation products have steep solubility curves so that when heavy suspensions thereof in cold water are warmed, they go through a pasty stage before giving clear solutions. In view of this an insufficient amount of water to give a clear solution when hot is introduced into the condensation product and upon cooling it rapidly goes through the pasty and then into the solid state to form a dry coherent body even though a substantial amount of water is present therein.

Although the invention has been described setting forth several specific embodiments thereof, the invention is not to be limited thereto as various changes in the details of operation and of composition may be made without departing from the principles herein set forth. For instance, instead of using the sodium salt of the [hydroxyethylsulphuric] *hydroxyethylsulphonic* acid, other soluble salts may be used, as for example, the potassium salt. Such substitution may be made in any of Examples 1 to 4. The acids used in the reaction may come from other sources than coconut oil and such sources may be vegetable, animal or synthetic. Other higher fatty acids than those specifically named may be substituted in part or in whole for the lauric and stearic fractions set forth in the specific examples. The proportions of the constituents may be varied to some degree and the excess thereof may be removed in a suitable manner or may be allowed to remain in the final product in such cases where the presence of the excess is not detrimental. The time, temperature and pressure of operation may be varied in co-relation so as to give the same results as set forth in Examples 1 and 2.

These and other changes in the details of the invention may be made within the scope thereof and the invention is, therefore, to be broadly construed and not to be limited except by the character of the claims appended hereto.

We claim:

1. A method of making detergents which comprises mixing 1 mol. of a water-soluble [hydroxyethylsulphuric] *hydroxyethylsulphonic* acid salt with an amount of a higher fatty acid less than 1 and more than 0.6 mol., maintaining an inert atmosphere, heating said mixture to a temperature of 200°–300° C. for a sufficient length of time to cause a substantial reaction to occur between said substances, the pressure being below atmospheric but above 250 mm., thereafter decreasing the pressure to below 100 mm., continuing the heating to remove free fatty acid.

2. A method of making detergents which comprises mixing 1 mol. of a water-soluble [hydroxyethylsulphuric] *hydroxyethylsulphonic* acid salt with an amount of a higher fatty acid less than 1 and more than 0.6 mol., maintaining an inert atmosphere, heating said mixture to a temperature of 230°–300° C. at a pressure below atmospheric but above 250 mm. for a sufficient length of time to cause a substantial reaction to occur between said substances, thereafter decreasing the pressure to below 100 mm., continuing the heating to remove free fatty acid.

3. A method of making detergents which comprises mixing 1 mol. of a water-soluble [hydroxyethylsulphuric] *hydroxyethylsulphonic* acid salt with an amount of a fatty acid taken from the class consisting of lauric, myristic, palmitic and stearic less than 1 and more than 0.6 mol., maintaining an inert atmosphere, heating said mixture to a temperature of 230°–300° C. for a sufficient length of time to cause a substantial reaction to occur between said substances, the pressure being below atmospheric but above 250 mm., thereafter decreasing the pressure to below 100 mm., continuing the heating to remove free fatty acid.

4. A method of making detergents which comprises mixing 1 mol. of a water-soluble [hydroxyethylsulphuric] *hydroxyethylsulphonic* acid salt with an amount of a higher fatty acid less than 1 and more than 0.6 mol., maintaining an inert atmosphere, heating said mixture to a temperature of 230°–300° C. for a sufficient length of time to cause a substantial reaction to occur between said substances, the pressure being below atmospheric but above 250 mm., thereafter decreasing the pressure to below 100 mm., continuing the heating to remove free fatty acid, and recrystallizing the product so formed to remove excess of said [hydroxyethylsulphuric] *hydroxyethylsulphonic* acid salt.

5. The reaction product of 1 mol. of a water-soluble [hydroxyethylsulphuric] *hydroxyethylsulphonic* acid salt with about 0.6 to 0.95 mol. of a higher fatty acid, produced by heating said reactants at 200°–300° C. at pressures below atmospheric and above 250 mm. in an inert atmosphere, and thereafter continuing said heating at pressures below 100 mm.

6. The reaction product of 1 mol. of a water-soluble [hydroxyethylsulphuric] *hydroxyethylsulphonic* acid salt with about 0.6 to 0.95 mol. of a higher saturated fatty acid, produced by heating said reactants at 200°–300° C. at pressures below atmospheric and above 250 mm. in an inert atmosphere, and thereafter continuing said heating at pressures below 100 mm.

7. The reaction product of 1 mol. of a water-soluble [hydroxyethylsulphuric] *hydroxyethylsulphonic* acid salt of an alkali metal with about 0.6 to 0.95 mol. of a fatty acid, produced by heating said reactants at 200°–300° C. at pressures below atmospheric and above 250 mm. in an inert atmosphere, and thereafter continuing said heating at pressures below 100 mm.

8. The reaction product of 1 mol. of a water-soluble [hydroxyethylsulphuric] *hydroxyethylsulphonic* acid salt with about 0.6 to 0.95 mol. of a higher fatty acid in the form of its alkali metal salt, produced by heating said reactants at 200°–300° C. at pressures below atmospheric and above 250 mm. in an inert atmosphere, and thereafter continuing said heating at pressures below 100 mm.

References Cited in the file of this patent or the original patent

UNITED STATES PATENTS

| Number | Name | Date |
|---|---|---|
| 2,175,285 | Duncan | Oct. 10, 1939 |
| 2,204,433 | Muncie et al. | June 11, 1940 |